(12) United States Patent
Cha et al.

(10) Patent No.: US 11,493,521 B2
(45) Date of Patent: Nov. 8, 2022

(54) KIT FOR TRACKING AND DIAGNOSING DEGREE OF PROGRESSIVE CHRONIC HEPATITIS AND LIVER FIBROSIS BY MEASURING ASIALO (ALPHA)1-ACID GLYCOPROTEIN AS HEPATOCELLULAR INJURY MARKER AND USE THEREOF

(71) Applicant: ACEBiomed, Inc., Jinju (KR)

(72) Inventors: WangJo Cha, Gwacheon (KR); Hyunhyo Suh, Jinju (KR); Mikyung Chung, Gwangmyeong (KR); Jae-hyun Cho, Seoul (KR); Mi Sook Jeong, Seoul (KR); Dahee Yoon, Seoul (KR); Myung Hun Lee, Ansan (KR); Sunghong Kim, Seoul (KR); Pil Sang Park, Suwon (KR)

( * ) Notice: Subject to any disclaimer, the term of this patent is extended or adjusted under 35 U.S.C. 154(b) by 225 days.

(21) Appl. No.: 16/746,814

(22) Filed: Jan. 18, 2020

(65) Prior Publication Data
US 2021/0132082 A1    May 6, 2021

(30) Foreign Application Priority Data
Oct. 31, 2019 (KR) .................. 10-2019-0137315

(51) Int. Cl.
  *G01N 33/68* (2006.01)

(52) U.S. Cl.
CPC . *G01N 33/6893* (2013.01); *G01N 2333/4724* (2013.01); *G01N 2333/4728* (2013.01); *G01N 2400/02* (2013.01); *G01N 2800/085* (2013.01)

(58) Field of Classification Search
None
See application file for complete search history.

(56) References Cited

FOREIGN PATENT DOCUMENTS

| KR | 2015-0041626 A | 4/2015 |
|---|---|---|
| KR | 10-1606302 B | 3/2016 |

*Primary Examiner* — Ellen J Marcsisin (57) ABSTRACT

Exemplary embodiments of the present invention relate to rapidly and easily test initial liver disease and more particularly to a monoclonal antibody for α1-acid glycoprotein, a diagnosis kit for tracking progressive chronic hepatitis and liver fibrosis in an initial phase of liver disease by measuring the concentration of asialo-α1-acid glycoprotein (AsAGP) as a hepatocyte injury marker in a sample using the antibody, and a use thereof.

Further, embodiments of the present invention provide a kit for specifically determining the degree of progressive chronic hepatitis and hepatic fibrosis from a blood sample and an immunochromatography strip, comprising a HRP-RCA II (Ricinus communis agglutinin II) conjugate or a Gold-RCA II conjugate specifically binding to asialo α-1 acid glycoprotein.

5 Claims, 7 Drawing Sheets

FIG. 1

FIG. 2

| Fibrosis stage | HBV(n=48) | | P-value |
|---|---|---|---|
| | n(%) | AsAGP | |
| Each fibrosis stage | | | |
| F0 | 20(41.7) | 1.36±0.25 | |
| F1 | 16(33.3) | 1.40±0.28 | |
| F2 | 2(4.2) | 1.29±0.22 | 0.014* |
| F3 | 2(4.2) | 1.40±0.04 | |
| F4 | 8(16.7) | 1.77±0.34 | |
| Advanced fibrosis | | | |
| F0-2 (chronic hepatis) | 38(79.2) | 1.37±0.26 | 0.002 |
| F3-4 (advanced fibrosis) | 10(20.8) | 1.69±0.34 | |
| Liver cirrhosis | | | |
| F0-3 (chronic hepatitis) | 40(83.3) | 1.38±0.25 | <0.001 |
| F4 (liver cirrhosis) | 8(16.7) | 1.77±0.34 | |

FIG. 3

| Diagnostic index | F3-4 | F4 |
|---|---|---|
| AUC | 0.788 | 0.825 |
| 95% CI | 0.647-0.930 | 0.674-0.976 |
| P-value | 0.005 | 0.004 |
| Cutoff value | 1.31 | 1.55 |
| sensitivity | 100.0% | 75.0% |
| specificity | 52.6% | 80.0% |

HBV : hepatitis B virus,   AUC : area under curve

FIG. 4

| Diagnostic index | F3-4 | | | | |
|---|---|---|---|---|---|
| cutoff value | 1.310 | 1.325 | 1.335 | 1.345 | 1.355 |
| sensitivity | 100.0% | 90.0% | 80.0% | 80.0% | 80.0% |
| specificity | 52.6% | 52.6% | 55.3% | 57.9% | 60.5% |

FIG. 5

Advanced fibrosis stage(F3-4)    Cirrhosis stage(F4)

FIG. 6

FIG. 7

1) Fibrosis stage 0, 2) Fibrosis stage 1, 3) Fibrosis stage 2
4) Fibrosis stage 3, 5) Fibrosis stage 4

KIT FOR TRACKING AND DIAGNOSING DEGREE OF PROGRESSIVE CHRONIC HEPATITIS AND LIVER FIBROSIS BY MEASURING ASIALO (ALPHA)1-ACID GLYCOPROTEIN AS HEPATOCELLULAR INJURY MARKER AND USE THEREOF

CROSS-REFERENCE TO RELATED APPLICATIONS

This application claims priority from and the benefit of Korean Patent Application No. 10-2019-0137315, filed on Oct. 31, 2019, which is hereby incorporated by reference for all purposes as if fully set forth herein

BACKGROUND

Technical Field

The present application relates to a device and method for rapidly and easily examining initial liver disease. Particularly, the present application relates to a monoclonal antibody against α1-acid glycoprotein, a kit for tracking and diagnosing the degree of progressive chronic hepatitis and liver fibrosis in an initial phase of liver disease by measuring the concentration of asialo α1-acid glycoprotein (AsAGP) as a hepatocellular injury marker in a sample using the antibody, and a use thereof.

Discussion of the Related Art

For accurate early diagnosis of various serious diseases including cancer, various serological biomarkers are used for health screening, and research to find better serological biomarkers has been conducted. Liver biopsy is a standard diagnostic method for diagnosing liver fibrosis, but there is a problem of accuracy due to errors in tissue collections, and there is a limit to the use in checking liver disease due to the risks that may arise in an invasive procedure, complications, and differences in proficiency among inspectors. In particular, postoperative pain is relatively common, and deaths associated with testing have also been reported. Due to the many problems caused by liver biopsy, doctors to conduct liver tissue biopsy or patients undergoing liver tissue biopsy are reluctant, and liver tissue biopsy is more difficult when repeated tests are needed. In addition, there is a problem that diagnosis is difficult without obtaining sufficient liver tissues. Due to this invasive problem, non-invasive models for predicting hepatic fibrosis have been developed.

Alternative methods include abdominal ultrasonography, a serum test using serum markers, etc. and currently, a liver elasticity test using liver fibrosis scan has been used as a non-invasive measure of liver fibrosis.

Hepatic cells have a strong regeneration function even if there is a disorder, and if about 20% to 30% of the whole tissues is normal, healthy parts has a characteristic of maintaining nearly normal functions and do not have abnormalities in a liver function test in mild lesions in case of serological liver disease diagnosis. In many test results, interrelationship is often not shown and thus a comprehensive review of the tests is required. It is not easy to predict the progression of severe fibrosis or cirrhosis in patients with chronic liver disease, and liver biopsy, which is used as a standard test method, may cause complications related to the procedure as an invasive method.

A liver elasticity test using liver fibroscan has an advantage of evaluating liver fibrosis by measuring liver elasticity non-invasively, but has a problem in that measurement is impossible when an elastic wave does not reach hepatic cells according to a physical condition of the patient or when the location of a wave probe is wrong. Further, a liver elasticity test is difficult depending on the age or a high body mass index of the tester.

Due to these problems, research on how to diagnose a liver fibrosis stage using several new serological biomarkers has been conducted, and it is required to develop diagnostic reagents by a new serological biomarker with high clinical efficacy capable of accurately diagnosing a liver fibrosis stage.

Chronic liver disease is a serious disease with a poor prognosis that can lead to cirrhosis in the future, and a disease with a high mortality rate relative to incidence. In particular, the incidence of the chronic liver disease is high in Asia including Korea, where the hepatitis virus infection rate is high. Therefore, the evaluation of the degree of hepatic fibrosis is very important for early diagnosis of chronic liver disease.

In chronic hepatitis, hepatic fibrosis occurs when hepatocellular inflammation and necrosis persist, and fibrosis is further progressed to cause cirrhosis. In order to more accurately evaluate and diagnose the degree of liver fibrosis in the progression of chronic liver disease, it is required to develop a hepatic elasticity test (FibroScan, magnetic resonance elastography (MRE)) for measuring the degree of liver fibrosis by a liver elasticity test, which has been currently used, and complementary serological liver fibrosis diagnostic biomarkers.

The developed hepatocellular injury biomarker, asialo α-1 acid glycoprotein (AsAGP), has high specificity for tracking and testing the degree of progressive chronic hepatitis and hepatic fibrosis, and is estimated to be available as a marker with very high clinical efficacy for the diagnosis and treatment of patients with chronic liver disease.

In the related art, there is a known method of diagnosing cirrhosis and liver cancer far beyond the progression of chronic hepatitis by measuring the concentration of asialo α-1 acid glycoprotein in the blood, but the related art has a problem that it is difficult to diagnose the degree of chronic hepatitis and liver fibrosis, which are the initial progression of the liver disease targeted in the present invention as a method for diagnosing only when the degree of liver disease should progress to liver cancer.

In order to solve the above problems, the inventors of the present invention found that the asialo α-1 acid glycoprotein has excellent specificity even in early liver disease, and completed the present invention in a process of finding a method capable of accurately diagnosing a progression stage of chronic hepatitis and liver fibrosis before the progression of liver disease to liver cancer.

Therefore, a method for diagnosing liver disease using asialo α-1 acid glycoprotein provided in the present invention is an excellent invention capable of preventing liver disease before the disease of the patient is expanded to the severe disease by early finding liver disease before the progression of the liver disease to the stage of cirrhosis and liver cancer.

SUMMARY

Various embodiments of the present invention are derived to solve the problems as discussed above. In accordance with various embodiments of the present invention, in order to track and diagnose the progression of progressive chronic hepatitis and liver fibrosis, a monoclonal antibody AGP601 specific to asialo α-1 acid glycoprotein (AsAGP) is used as a capture protein to configure a conjugate of *Ricinus communis* agglutinin II (RAC II) and active horseradish peroxidase (HRP) which are cognitive proteins of asialo α-1 acid glycoprotein as a searching protein, and in order to confirm the degree of liver fibrosis, serums of patients with liver disease are analyzed by comparing fibrosis stages.

Efficacy evaluation variables of the present invention include sensitivity and specificity for the evaluation of the degree of liver fibrosis for each fibrosis stage using a liver fibroscan method as a standard model, and as a result, a positive result for a positive sample and a negative result for a negative sample are evaluated.

When comparing the degree of liver fibrosis according to the result of the efficacy evaluation, the blood AsAGP concentration increased as the fibrosis became more severe, and even in a result of a difference in the mean AsAGP concentration for each liver fibrosis stage, it was found that a p-value was significant as 0.0414, and it was confirmed that this could be used as an index to predict the degeneration of progressive chronic hepatitis.

Therefore, embodiments of the present invention are proposed by confirming that the progression of chronic hepatitis and hepatic fibrosis can be tracked and diagnosed with blood when using a monoclonal antibody AGP601 and a RCA II-HRP conjugate to α-1 acid glycoprotein according to embodiments of the present invention.

Embodiments of the present invention provide a method of measuring a concentration of asialo α-1 acid glycoprotein in the blood comprising:

(a) adsorbing to a solid body a monoclonal antibody AGP601 against asialo α-1 acid glycoprotein produced by a fused cell line deposited with the accession number KCTC13998BP;

(b) adding a blood sample containing the asialo α-1 acid glycoprotein to the solid body to which the monoclonal antibody AGP601 against the asialo α-1 acid glycoprotein is adsorbed in step (a) to bind the asialo α-1 acid glycoprotein to the monoclonal antibody AGP601;

(c) adding and binding a HRP (horseradish peroxidase)-RCA II (Ricinus communis agglutinin II) conjugate specifically bound to the asialo α-1 acid glycoprotein to the asialo α-1 acid glycoprotein bound to the monoclonal antibody AGP601 against the asialo α-1 acid glycoprotein produced by the fused cell line deposited with the accession number KCTC13998BP; and (d) measuring and analyzing the concentration of the asialo α-1 acid glycoprotein.

By the method of measuring the concentration of asialo α-1 acid glycoprotein in the blood according to embodiments of the present invention, it is possible to specifically and accurately determine the degree of progressive chronic hepatitis and hepatic fibrosis in a patient.

Further, embodiments of the present invention provide a kit for specifically determining the degree of progressive chronic hepatitis and hepatic fibrosis from a blood sample and an immunochromatography strip, comprising a HRP-RCA II (Ricinus communis agglutinin II) conjugate or a Gold-RCA II conjugate specifically binding to asialo α-1 acid glycoprotein in which the monoclonal antibody AGP601 against the asialo α-1 acid glycoprotein produced by the fused cell line deposited with the accession number KCTC13998BP and horseradish peroxidase (HRP) are bound to each other or bound with gold-nano particles.

In embodiments of the present invention, an antibody AGP601 (KCTC13998BP) against α-1 acid glycoprotein and RCA II specifically binding to asialo α-1 acid glycoprotein are isolated and purified, and it is possible to early track and diagnose the degree of progressive chronic hepatitis and hepatic fibrosis by the antibody AGP601 and the RCA II-HRP conjugate selectively isolated and purified as described above.

Based on this, the progressive chronic hepatitis and hepatic fibrosis can be tracked and diagnosed to facilitate the early detection and treatment of chronic liver disease, thereby preventing the progression to fatal cirrhosis and liver cancer. Currently, there is no serological test method to accurately track and diagnose the degree of liver fibrosis in the progression of chronic liver disease. Therefore, it is conventionally necessary to develop a diagnostic biomarker of serological liver fibrosis complementary with FibroScan, which is a diagnostic medical device for measuring the degree of liver fibrosis by a liver elasticity test at medical institutions domestically and abroad.

The technology of the present invention will play a significant role in the development of related industries such as human health promotion and medical devices when widely used in specialized medical institutions as a technology capable of tracking and diagnosing the degree of progressive chronic hepatitis and liver fibrosis.

BRIEF DESCRIPTION OF THE DRAWINGS

FIG. 1 shows results of confirming a monoclonal antibody against an anti-AGP antibody produced by a fused cell line of the present invention by SDS-PAGE and Western blotting.

FIG. 2 illustrates the statistical significance by analyzing a difference in AsAGP concentration for each fibrosis stage group.

FIG. 3 illustrates effectiveness through sensitivity, specificity, and AUC values to an advanced fibrosis stage of a Hepatitis B virus (HBV) chronic hepatitis subject.

FIG. 4 illustrates effectiveness according to a difference in cuttoff value of the HBV chronic hepatitis subject.

FIG. 5 is a graph showing results of analyzing efficacy evaluation variables for the track and diagnosis of the degree of progressive chronic liver disease and liver fibrosis by using a kit AsAGP using an anti-AGP antibody AGP601 and a RCA II-HRP conjugate according to the present invention.

FIG. 6 illustrates a plan view and a front view of an immunochromatography strip provided in the present invention.

FIG. 7 illustrates results of measuring concentrations of asialo α-1 acid glycoprotein measured by the immunochromatography strip according to the present invention.

DETAILED DESCRIPTION OF EMBODIMENTS

In general, cirrhosis such as liver disease is a disease that is deepened in the initial symptoms such as chronic hepatitis or liver fibrosis and finally metastasized to liver cancer. Most of known methods for diagnosing liver disease are limited to methods for diagnosing liver cirrhosis or liver cancer, which are the final stages. This is because in a diagnosis method using image diagnosis or a tracer present in the blood, when liver disease reaches significantly metastasized liver cirrhosis or liver cancer, the content of biomarkers capable of determining the liver disease is significantly accumulated to be accurately determined as liver cirrhosis or liver cancer when comparing the content of the biomarkers with health liver.

On the other hand, in the case of chronic hepatitis or liver fibrosis, which is an early stage of liver disease, this is because soon after the metastasis of liver disease, the content of the biomarkers is insufficient, and thus the accuracy in determining chronic hepatitis or liver fibrosis is significantly low even using imaging diagnosis or a general tracer.

Hepatic cells have a strong regeneration function even if there is a disorder, and if about 20% to 30% of the whole tissues are normal, healthy parts have a characteristic of maintaining nearly normal functions and do not have abnormalities in a liver function test in mild lesions in case of serological liver disease diagnosis. In the early stages of the lesion, in many test results, interrelationship is often not shown and thus early lesions, such as chronic hepatitis or liver fibrosis, are difficult to be determined by conventional diagnostic reagents or diagnosing methods.

In addition, it is difficult to predict progression to severe fibrosis or cirrhosis in patients with chronic liver disease, liver biopsy as an invasive method may cause complications associated with a procedure, and a liver elasticity test using a liver fibroscan has an advantage of evaluating liver fibrosis by non-invasively measuring liver elasticity, but there is a problem that it may be difficult to measure the liver elasticity depending on a physical condition or an age of a patient and a body mass index.

Due to these problems, various studies on the method of diagnosing a liver fibrosis stage using a new serological biomarker have been conducted. In this situation, the inventors of the present invention have found that in order to diagnose chronic hepatitis or liver fibrosis which is a disease of an early stage of liver disease as described above, various biomarkers and the like have been used, and as a result, the asialo α-1 acid glycoprotein according to embodiments of the present invention is a tracer to determine liver disease in the most suitable early stage, and completed the present invention.

There are many methods of qualitatively or quantitatively analyzing specific substances such as asialo α-1 acid glycoprotein, but among these methods, particle agglutination assays, radioimmunoassays (RIA), enzyme immunoassays (EIA), fluoroimmunoassays (FIA), etc. have been most widely used. Among these methods, the RIA has high sensitivity, but has many problems according to the use of a radiolabel, and thus EIA and FIA which have high sensitivity and are safe and simple have been more commonly used. In the EIA, generally, enzymes having high safety, such as alkaline phosphatase, horseradish peroxidase, and glucose oxidase, are used and as a substrate of the enzyme, a color substance having a high turn-over rate is selected and used. This method has sensitivity and specificity similar to the RIA and has been widely used by solving the shortcomings of RIA.

The present inventors developed a sandwich type measurement method using an antibody against α-1 acid glycoprotein and lectin that recognizes asialo glycoprotein and a measuring kit for the same as a measuring method and a kit capable of measuring a plurality of samples at the same time with high safety and reproducibility as compared with existing methods of measuring a concentration of asialo α-1 acid glycoprotein, thereby effectively measuring a blood concentration of asialo α-1 acid glycoprotein using the same.

The method of measuring the asialo α-1 acid glycoprotein provided in exemplary embodiments of the present invention to achieve one or more objects of the present invention comprises:

(a) adsorbing to a solid body a monoclonal antibody AGP601 against asialo α-1 acid glycoprotein produced by a fused cell line deposited with the accession number KCTC13998BP;

(b) adding a blood sample containing the asialo α-1 acid glycoprotein to the solid body to which the monoclonal antibody AGP601 against the asialo α-1 acid glycoprotein is adsorbed in step (a) to bind the asialo α-1 acid glycoprotein to the monoclonal antibody AGP601;

(c) adding and binding a HRP (horseradish peroxidase)-RCA II (Ricinus communis agglutinin II) conjugate specifically bound to the asialo α-1 acid glycoprotein to the asialo α-1 acid glycoprotein bound to the monoclonal antibody AGP601 against the asialo α-1 acid glycoprotein produced by the fused cell line deposited with the accession number KCTC13998BP; and (d) measuring and analyzing the concentration of the asialo α-1 acid glycoprotein.

Yet another object of the present invention provides a measuring method of asialo α-1 acid glycoprotein using a kit and an immunochromatography strip containing a monoclonal antibody AGP601 against α-1 acid glycoprotein prepared to measure the content of asialo α-1 acid glycoprotein included in the blood, which comprises the above-noted steps.

More specifically, the method of the present invention may be performed, for example, as follows. An antibody against α-1 acid glycoprotein is added to a solid body such as a microtiter platewell, left for 1 hour or more, adsorbed onto the microtiter platewell, and then reacted at room temperature by adding a dilute serum sample solution to each well. After the reaction, lectin labeled with an enzyme or a fluorescent material, for example, an HRP-RCA II conjugate is added to each well and reacted at room temperature. After the well is washed with a washing solution, a color development substrate of the enzyme, for example, an ortho-phenylene diamine substrate solution is added to each well to develop a color. After a predetermined time, the reaction is stopped, the absorbance is measured at an appropriate wavelength, and the concentration of asialo α-1 acid glycoprotein in blood is calculated by comparing the measured absorbance with absorbance of an asialo α-1 acid glycoprotein standard solution. When the labeling substance is a fluorescent substance, lectin labeled with a fluorescent substance is added to each well, reacted at room temperature, and then washed with a washing solution, and fluorescence intensity is measured.

The measuring method of the asialo α-1 acid glycoprotein provided by the present invention uses a sandwich immunoassay using an antibody against α-1 acid glycoprotein and lectin in order to measure the concentration of asialo α-1 acid glycoprotein estimated to be formed in an excessive amount in the blood when progressive chronic hepatitis and liver fibrosis are advanced.

In other words, the sandwich immunoassay provided in exemplary embodiments of the present invention described above comprises (a) binding a monoclonal antibody AGP601 against asialo α-1 acid glycoprotein to a solid body such as a microtiter plate, (b) adding a blood sample containing the asialo α-1 acid glycoprotein to the solid body to bind the asialo α-1 acid glycoprotein to the monoclonal antibody AGP601, (c) adding a RCA II-HRP conjugate bound with HRP as a labeling substance to bind the conjugate to the asialo α-1 acid glycoprotein bound to the antibody, and (d) detecting the RCA II-HRP conjugate as the labeling substance to measure the concentration of the asialo α-1 acid glycoprotein.

The monoclonal antibody AGP601 against the α-1 acid glycoprotein according to exemplary embodiments of the present invention may be prepared from fused cells KCTC13998BP deposited with the Korea Research Institute of Bioscience and Biotechnology.

In addition, exemplary embodiments of the present invention use an RCA II-HRP conjugate prepared by selectively isolating and purifying a lectin protein and a RCA II protein that specifically recognize asialo α-1 acid glycoprotein.

In the method according to an embodiment of the present invention, the blood sample may be blood collected from a patient suspected of progressive chronic hepatitis and liver fibrosis, but is not limited thereto.

Further, exemplary embodiments of the present invention provide a kit for tracking and diagnosing progressive chronic hepatitis and liver fibrosis from a blood sample, comprising an HRP-RCA II (Ricinus communis agglutinin II) conjugate specifically binding to asialo α-1 acid glycoprotein, in which a monoclonal antibody AGP601 against α-1 acid glycoprotein produced by a fused cell line deposited to accession number KCTC13998BP is bound to horseradish peroxidase (HRP).

Exemplary embodiments of the present invention provide a kit for tracking and diagnosing progressive chronic hepatitis and liver fibrosis, a kit comprising a RCA II-HRP conjugate specifically binding to asialo α-1 acid glycoprotein, in which a solid body to which a monoclonal antibody AGP601 against α-1 acid glycoprotein is bound to a labeling substance HRP.

The kit according to exemplary embodiments of the present invention may further comprise an ortho-phenylenediamine (OPD) substrate solution, a phosphate buffer and a serum diluent with Tween as a washing solution, and an asialo α-1 acid glycoprotein standard solution in addition to the RCA II-HRP conjugate specifically binding to the asialo α-1 acid glycoprotein, in which the solid body to which the monoclonal antibody AGP601 against α-1 acid glycoprotein is bound to the labeling substance HRP, but is not limited thereto.

As yet another diagnosing method, exemplary embodiments of the present invention provide an immunochromatography strip comprising a Gold-RCA II conjugate which is a conjugate of a monoclonal antibody reacting specifically to α-1 acid glycoprotein and lectin recognizing asialo glycoprotein, which is useful to rapidly and simply test possibility of chronic liver disease and liver fibrosis by measuring the concentration of asialo α-1 acid glycoprotein in a blood sample.

Exemplary embodiments of the present invention provide an immunochromatography strip comprising a monoclonal antibody AGP601 produced by a fused cell line disclosed as accession number KCTC13998BP and the HRP-RCA II (Ricinus communis agglutinin II) conjugate or a goldnano-RCA II conjugate. Exemplary embodiments of the present invention provide an immunochromatography strip comprising a glass fiber (GF) pad to which the RCA II of the present invention described above and gold colloid are conjugated, a nitrocellulose (NC) membrane in which a control line and a determination line of a result of detecting asialo α-1 acid glycoprotein are linearly processed, a sample pad which is a part absorbing a sample to be tested, an absorbent pad absorbing a non-react material in the sample, and an adhesive plastic backing to which the aforementioned members are mounted.

In the immunochromatography strip according to exemplary embodiments of the present invention, the NC membrane, the GF pad, the sample pad, and the absorbent pad are sequentially mounted on the adhesive plastic backing and assembled so that materials may be continuously moved by a capillary phenomenon. The method of assembling the immunochromatography strip may be performed according to a general strip preparing method. An immunochromatography strip according to exemplary embodiments of the present invention may be prepared in the form of a cassette or in the form of a stick.

Hereinafter, the present invention will be described in detail by Examples. However, the following Examples are just illustrative of the present invention, and the contents of the present invention are not limited to the following Examples.

Example 1

Production of Monoclonal Antibody Specific to α-1 Acid Glycoprotein (AsAGP) and Preparation of RCA II-HRP Conjugate In order to screen fused cells reacting specifically to only α-1 acid glycoprotein (AGP), an α-1 acid glycoprotein antigen was added to a microplate by 100 μl per well, reacted for 2 hours, and then washed with a phosphate buffer-Tween 20 solution. After washing, ortho-phenylenediamine was added and reacted as a substrate solution of goat anti-mouse IgG-horseradish peroxidase to screen fused cell lines that secreted antibodies having a high binding force specifically to the α-1 acid glycoprotein antigen. The screened cell line AGP601 was deposited with accession number KCTC13998BP to the Korea Biotechnology Research Institute Gene Bank on Oct. 17, 2019.

Figure 1:
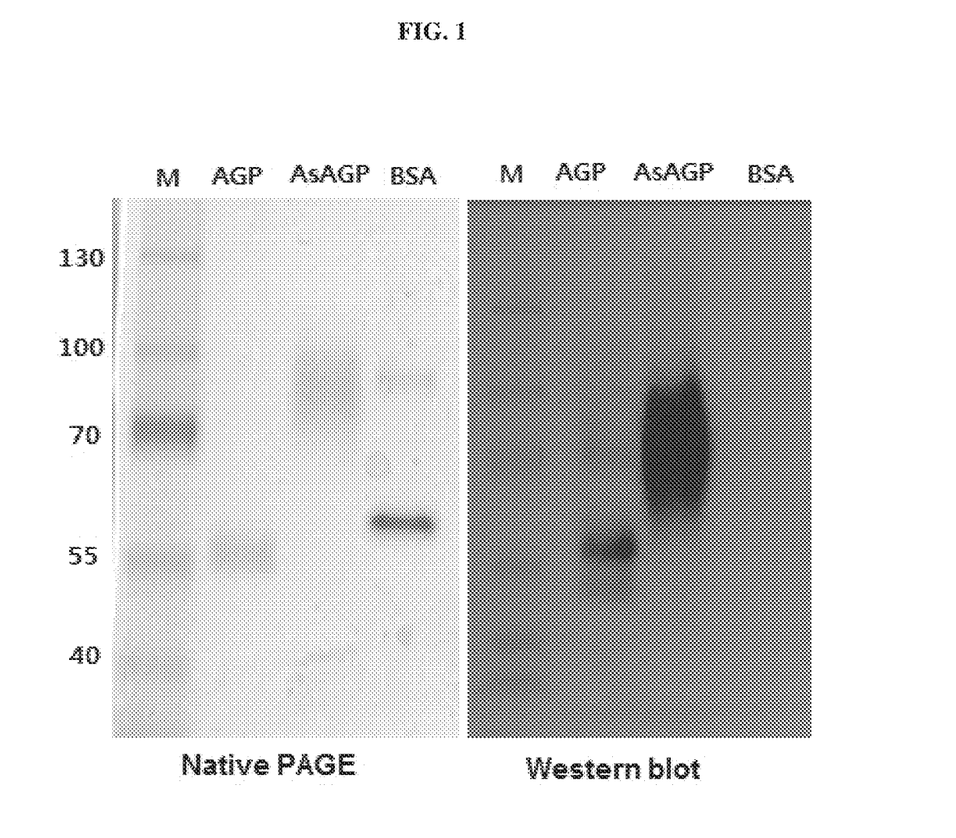

In order to mass-produce an AGP601 monoclonal antibody of subclass IgG2b of a fused cell line, 300 μl of an incomplete adjuvant was injected into the abdominal cavity of 8-week old Balb/c mice. After two weeks, hybridoma cells grown in an RPMI medium containing bovine serum were injected by 200 μl ($4\times10^6$/cells) per mouse, and an ascitic fluid was collected from mice in which the abdominal cavity was swollen. The collected ascitic fluid was centrifuged for each mouse serum to remove red blood cells, and then a supernatant was stored at −20° C. A specific antigen response of a monoclonal antibody specific to α-1 acid glycoprotein (AGP) isolated and purified by Protein A column chromatography was confirmed by performing protein electrophoresis and western blotting (FIG. 1).

The protein electrophoresis and the western blotting were performed according to methods known in the art. In addition, in the AGP 601 of the present invention, it was confirmed that the antigen response to an AsAGP antigen in a native form state was much higher than that of a previously known As16.89 monoclonal antibody and AGP501.

A lectin protein, RCA II protein isolated from castor seeds, was dialyzed with a 0.2 M sodium carbonate buffer ($NaHCO_3$, pH 8.3) at 4° C. for 18 hours, and then the concentration of the RCA II protein was measured, and active HRP (horseradish peroxidase) and the RCA II protein were mixed at a constant concentration ratio and reacted at room temperature for 3 hours. The mixture of the active HRP and RCA II proteins was kept in a brown glass bottle and reacted at 4° C. for 18 hours. After the reaction was completed, each mixture was added with 1 M triethanolamine and a 0.1 M sodium borohydride solution and reacted at 4° C. for 60 minutes, added with a reaction stopper and then stirred at 4° C. and the reaction was stopped. After the reaction was completed, the RCA II-HRP conjugate was dialyzed in a PBS buffer for about 18 hours to remove a reaction buffer and then stabilized by addition of 2 M glycine. The reaction solution stabilized as such was gel-filtered to separate the RCA II-HRP conjugate.

Example 2

Figure 2:
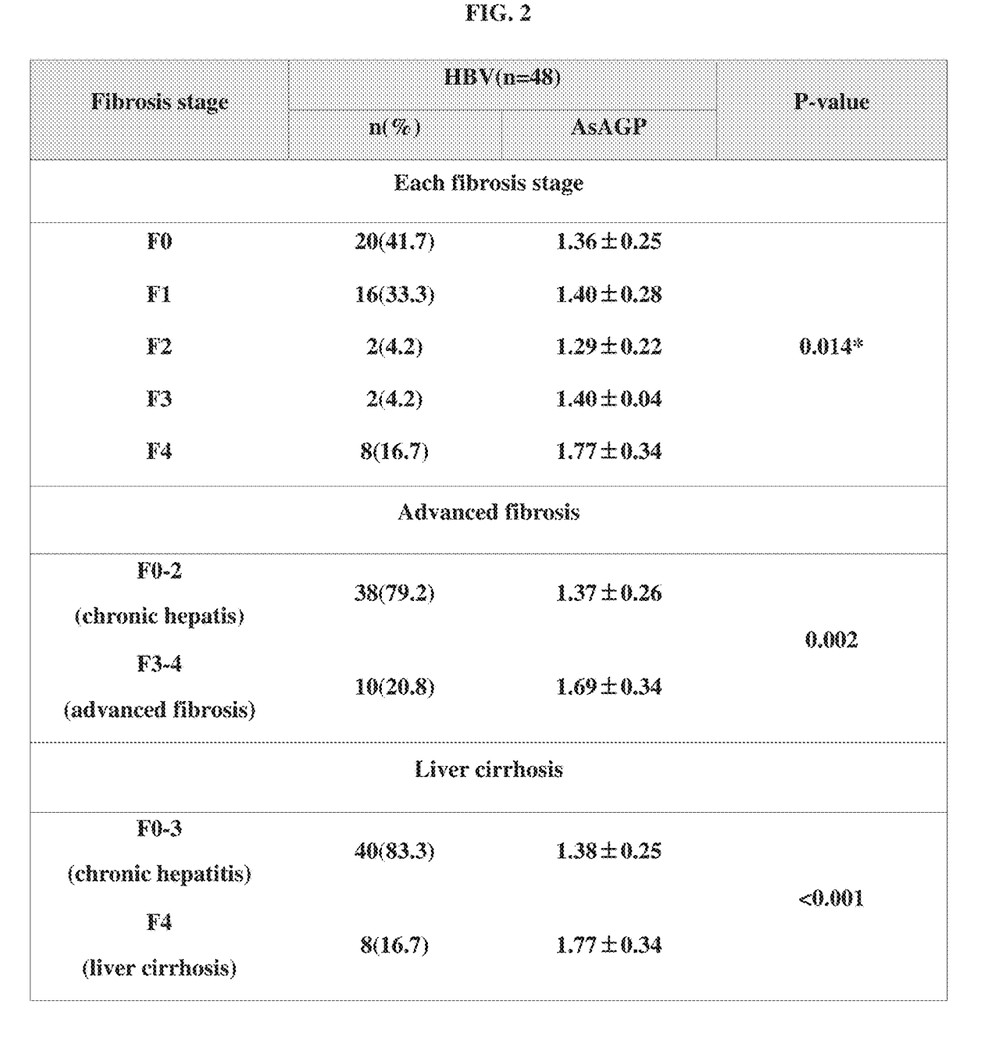

Analysis of Difference in Concentration of Asialo α-1 Acid Glycoprotein (AsAGP) in Each Fibrosis Stage liver fibrosis of a target subject was measured by a fibroscan, a diagnostic medical device for liver fibrosis, the RCA II protein and active HRP conjugate isolated in Example 1 was used as a search protein, an antibody AGP601 against α-1 acid glycoprotein (AsAGP) was composed of a capture protein, the concentration of asialo α-1 acid glycoprotein (AsAGP) in a blood sample of a patient suspected of progressive chronic liver disease and liver fibrosis was measured to measure a correlation with of asialo α-1 acid glycoprotein according to the degree of liver fibrosis, and the results thereof are illustrated in FIG. 2.

The results of analyzing the correlation between the degree of liver fibrosis, the concentration of AsAGP, and other variables were illustrated in FIG. 1. Among 48 persons determined as a HBV chronic hepatitis subject, fibrosis stage 0 was confirmed as 20 persons (41.7%), fibrosis stage 1 was confirmed as 16 persons (33.3%), fibrosis stage 1 and fibrosis stage 3 were confirmed as 2 persons (4.2%), respectively, and fibrosis stage 4 was confirmed as 8 persons (16.7%).

The mean of AsAGP concentrations in the subjects determined from fibrosis stage 0 (F0) to fibrosis stage 2 (F2) was 1.37±0.26, and the mean of AsAGP concentrations in the subjects determined from fibrosis stage 3 (F3) to fibrosis stage 4 (F4) was confirmed as 1.69±0.34. As a result of testing a difference in the mean AsAGP concentration between the two groups, the p-value was 0.002, indicating that the difference was statistically significant.

The mean of AsAGP concentrations in the subjects determined from fibrosis stage 0 (F0) to fibrosis stage 3 (F3) was 1.38±0.25, and the mean of AsAGP concentrations in the subjects determined to fibrosis stage 4 (F4) was confirmed as 1.77±0.34. As a result of testing a difference in the mean AsAGP concentration between the two groups, the p-value was <0.001, indicating that the difference was statistically significant.

These results showed that when comparing the degree of liver fibrosis according to a fibrosis stage, the blood AsAGP concentration increased as the fibrosis increased, and the p-value was significant as 0.014 as a result of testing the difference in the mean AsAGP concentration for each fibrosis stage.

Example 3

Figure 3:
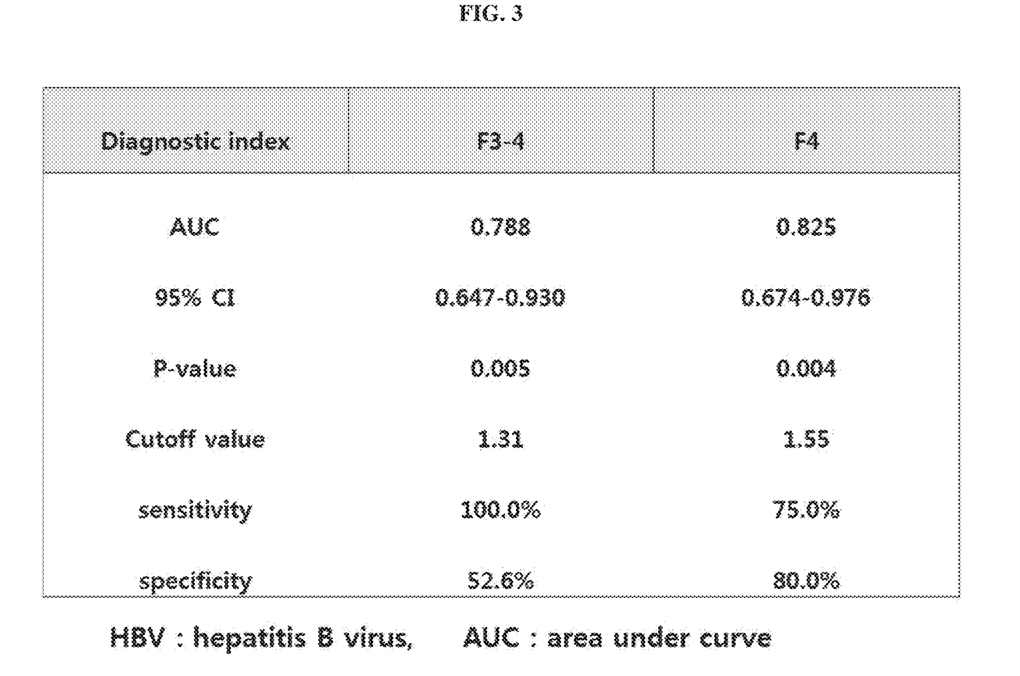

Prediction of Degree of Liver Fibrosis in Patients with HBV Chronic Hepatitis by Measuring Asialo α-1 Glycoprotein (AsAGP) Concentration The results of evaluating the effectiveness for each fibrosis stage of the subject patient according to exemplary embodiments of the present invention are illustrated in FIG. 3. The AUC values for advanced fibrosis stages (stages 3 to 4) and cirrhosis stage of HBV chronic hepatitis subjects were calculated and as a result, prediction of HBV chronic hepatitis fibrosis was an effective level as AUC>0.75, and an appropriate cutoff value was calculated to confirm a stage in which liver fibrosis corresponding to advance or cirrhosis was severely worsened.

Figure 4:
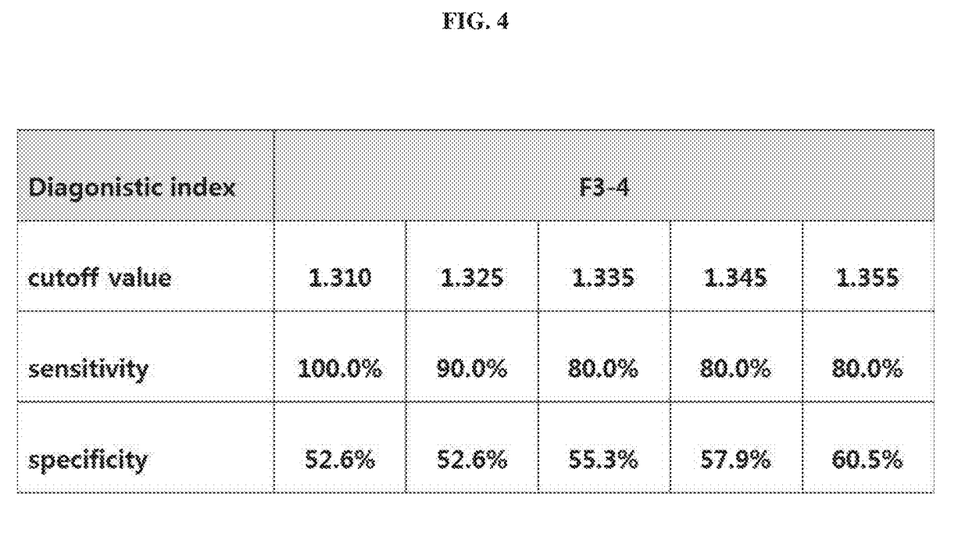

Secondary efficacy evaluation variables indicate the sensitivity and specificity to the degree of liver fibrosis for each fibrosis stage according to embodiments of the present invention, and as a result, a positive judgment for a positive sample and a negative judgment for a negative sample may be evaluated, and the results are illustrated in FIG. 4.

As illustrated in FIG. 4, in HBV chronic hepatitis patients, when the cutoff value, which was the standard for advanced fibrosis stages (stages 3 to 4), was set to 1.310, the sensitivity was 100% and the specificity was 52.6%, and a difference in sensitivity and specificity according to a cutoff value was increased until the cutoff value was 1.355, the sensitivity was 80% and the specificity was 60.5%. The specificity was originally derived from normal subjects, and in this study, the specificity is lower than the original specificity to distinguish liver fibrosis/liver cirrhosis to chronic hepatitis patients. In test results compared with a normal group, it was confirmed that the specificity increased by 84%.

Figure 5:
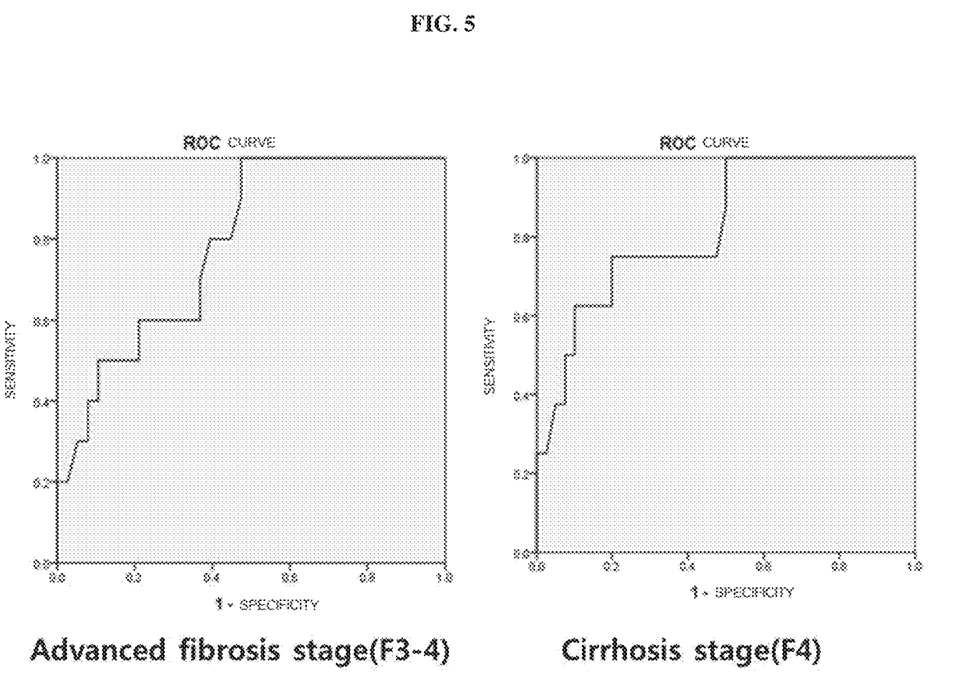

FIG. 5 shows that when the cutoff value was set to 1.310, the sensitivity was 100% and the specificity was 52.6% for HBV chronic hepatitis patients at advanced fibrosis stages (stages 3 to 4), and the sensitivity was 75% and the specificity was 80% at liver cirrhosis stage (stage 4), where HBV chronic hepatitis patients' liver fibrosis deteriorates to be serious. The results shown in FIG. 5 confirm that a kit using AsAGP according to embodiments of the present invention is useful in diagnosing seriousness of liver fibrosis for chronic hepatitis patients. (ROC stands for receiver operating characteristics; HBV stands for hepatitis B virus)

Example 4

Preparation of Immunochromatography Strip Comprising Monoclonal Antibody AGP601 Against α-1 Acid Glycoprotein (1) Preparation of RCA II Gold Conjugate 15 μg/ml of RCA II reactive to the asialo α-1 acid glycoprotein selected in embodiments of the present invention was added to a colloidal gold particle solution, and then reacted while rotating at room temperature for 2 hours, added with 10% BSA to 1/10 volume to be a concentration of 1% and then reacted again for 1 hour to prepare an Ab-gold conjugate. The mixture was centrifuged at 12,000 rpm for 10 minutes and a supernatant was removed, and the Ab-gold conjugate was washed by adding a 2 mM borate buffer again. The washing was performed three times. After the last washing, a 2 mM borate buffer containing 1% BSA was suspended by adding about 1/10 volume of the gold solution. After absorbance was measured at 530 nm with a UV spectrometer, the mixture was diluted and used so that the measured value become 3.00.

(2) Sample Pad

As a part for absorbing a sample to be tested, a sample pad made of a cellulose material was used.

(3) Glass Fiber (GF) Pad

As a part where an immune response between asialo α-1 acid glycoprotein in the sample and the RCA II prepared according to the present invention occurred, gold colloidal particles RCA II were temporarily immobilized on the surface of the GF membrane, and the preparation method was as follows.

Monoclonal antibodies produced from the prepared RCA II were conjugated as shown in (1) above.

The GF pad (produced from Milipore Co., Ltd., 1.0 cm×0.7 cm) was sufficiently wetted in a 20 mM sodium borate buffer and dried, and then the gold colloidal particulate-RCA II prepared above was evenly sprayed on the GF membrane and dried at 37° C. to prepare a GF pad (also referred to as a conjugate pad) for an immune response pad with colored particle solid-phase antibodies temporarily immobilized on the surface.

(4) Nitrocellulose (NC) Membrane and Line Treatment

After a nitrocellulose membrane (Millipore Co., Ltd.) was attached to a plastic backing (30 cm×5 cm), goat anti-mouse IgG was linearly treated as a control line at a point approximately 3.4 cm from the bottom of the plastic backing, asialo α-1 acid glycoprotein was detected at a point of 2.7 cm, and as a result, hybridoma cells AGP601 as a determination line were linearly treated and then dried to prepare an NC membrane.

(5) Absorbent Pad

A cellulose membrane was used to absorb unreacted substances in a sample after the immune response so that a sample solution containing an analyte is moved by capillary action.

(6) Preparation of Immunochromatography Strip

Figure 6:
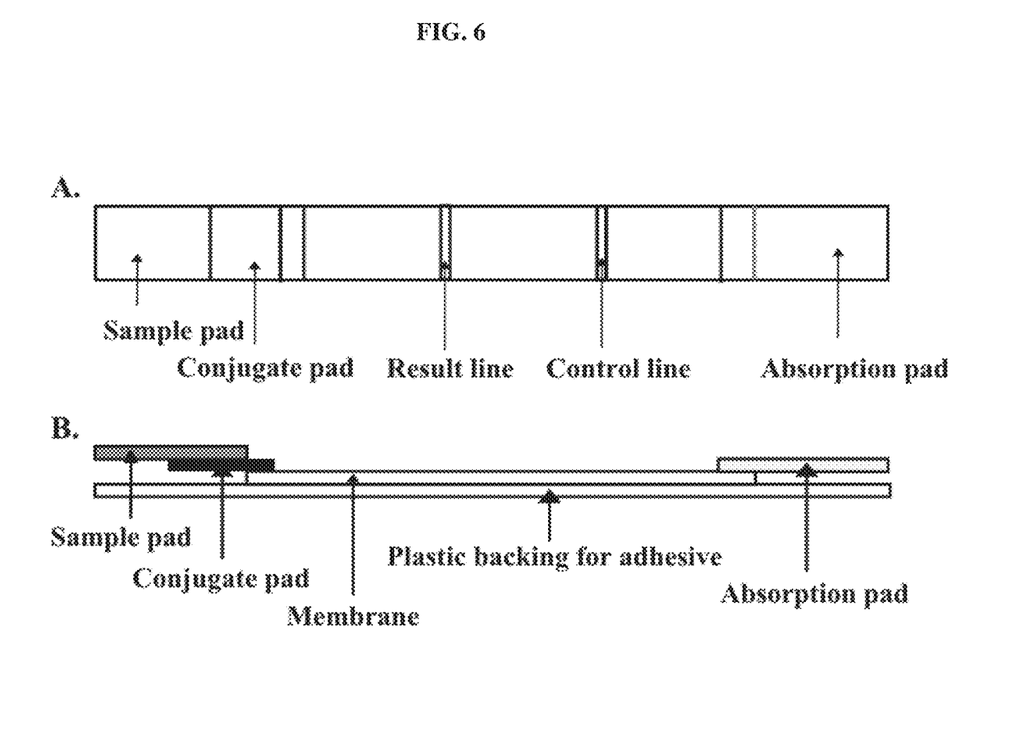

As illustrated in FIGS. 6A and 6B, the NC membrane, the GF pad, the sample pad, and the absorbent pad are sequentially mounted on the adhesive plastic backing, and arranged, assembled, and adhesively fixed to be partially overlapped by about 0.1 cm so that the materials may be continuously moved by capillary action.

Example 5

Analysis of Concentration of Asialo α-1 Acid Glycoprotein Using Immunochromatography Strip 60 μl to 70 μl of a serum sample solution diluted with an elution buffer (e.g., 50 mM borate buffer containing 5% sucrose, 1% bovine serum albumin (BSA) or 1% Triton™ X-100 surfactant) at a ratio of 1:10 was added in the sample pad of the immunochromatography strip prepared in Example 4, and after 3 to 5 minutes, the presence or absence of coloring of the control line and the determination line was observed.

Figure 7:
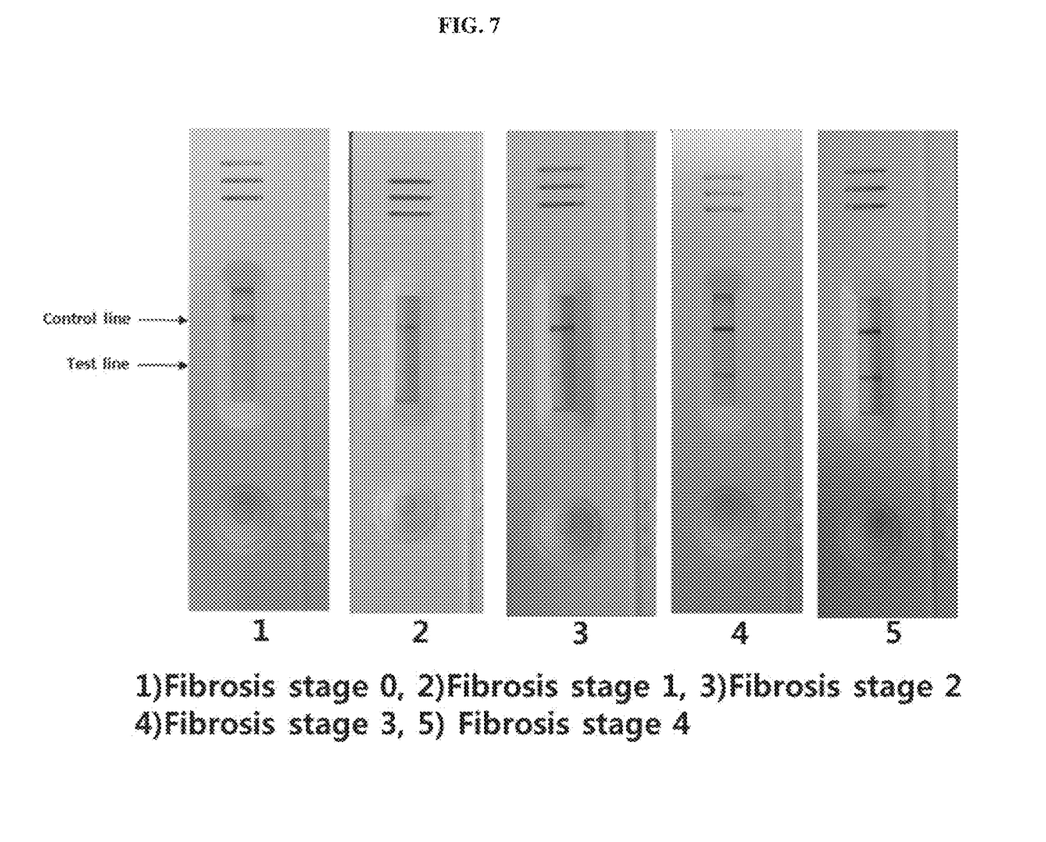

FIG. 7 illustrates results determined in a cassette-type immunochromatography strip. Line 1 is a strip applying serum corresponding to Fibrosis stage 0 (F0), and Lines 2 to 5 are strips applying serums according to the degree of liver fibrosis corresponding to Fibrosis stage 1 (F1) to Fibrosis stage 4 (F4). As can be seen from the above results, the coloration line is weak in line 2 corresponding to Fibrosis Stage 1, but in strips 4 and 5 (Fibrosis stage 3, Fibrosis stage 4, F4) in which the degree of liver fibrosis becomes severe, in a clear red coloration line was confirmed in the control line (upper line) and the detected determination line (lower line).

As can be seen from the above results, when using the diagnostic kit and the immunochromatography strip for immunoassay using the monoclonal antibody against the α-1 acid glycoprotein of the present invention, it is possible to early, quickly and easily diagnose chronic hepatitis and liver fibrosis, which are early stages of liver disease by diagnosing the significance of asialo α-1 acid glycoprotein in the blood simply and easily and prevent liver diseases by measuring or monitoring a progression degree of liver disease in an early stage before patients are metastasized to liver cancer which is a severe disease.

Therefore, the AsAGP diagnostic kit using the technology of the present invention may be applied as a useful test method for early diagnosis before progression to severe liver disease as a technology capable of tracking and diagnosing the progression of progressive chronic hepatitis and liver fibrosis.

Accession Number

Depositary Institute Name: Korea Research Institute of Bioscience and Biotechnology Accession number: KCTC13998BP Accession Date: Oct. 17, 2019

The invention claimed is:

1. A method for specifically determining degree of progressive chronic hepatitis and liver fibrosis, the method comprising:

adsorbing to a solid body a monoclonal antibody specific to α-1 acid glycoprotein, wherein the monoclonal antibody is monoclonal antibody AGP601 produced by a fused cell line deposited with the accession number KCTC13998BP;

adding a blood sample containing asialo α-1 acid glycoprotein to the solid body to which the monoclonal antibody AGP601 is adsorbed, wherein the asialo α-1 acid glycoprotein binds to the monoclonal antibody AGP601 forming an asialo α-1 acid glycoprotein-AGP601 complex;

adding and binding a conjugate to the asialo α-1 acid glycoprotein-AGP601 complex, wherein the conjugate is a *Ricinus communis* agglutinin II (RCA II) and horseradish peroxidase (HRP) conjugate (RCA II-HRP); and measuring concentration of the asialo α-1 acid glycoprotein by detecting binding between the conjugate and the complex, thereby determining the degree of progressive chronic hepatitis and liver fibrosis.

2. The method of claim 1, wherein the blood sample is a blood sample collected from a patient suspected of having progressive chronic hepatitis and liver fibrosis.

3. A kit for determining degree of progressive chronic hepatitis and liver fibrosis, the kit comprising: monoclonal antibody AGP601 produced by a fused cell line deposited with the accession number KCTC13998BP, and an HRP-RCA II (Ricinus communis agglutinin II) conjugate.

4. An immunochromatography strip for determining degree of progressive chronic hepatitis and liver fibrosis, the immunochromatography strip comprising: a monoclonal antibody AGP601 produced by a fused cell line deposited with the accession number KCTC13998BP, and a Gold nanoparticle-RCA II conjugate.

5. The immunochromatography strip of claim 4, wherein the immunochromatography strip is in the form of a cassette.

* * * * *